United States Patent [19]

Yamaguchi

[11] Patent Number: 4,921,560
[45] Date of Patent: May 1, 1990

[54] METHOD FOR FIXING PERMANENT MAGNETS TO COVER OF BEDCLOTHING

[75] Inventor: Tomoyoshi Yamaguchi, Tokyo, Japan

[73] Assignee: J. L. S. Corp., Tokyo, Japan

[21] Appl. No.: 105,336

[22] Filed: Oct. 6, 1987

[30] Foreign Application Priority Data

Jun. 18, 1987 [JP] Japan .............................. 62-152101

[51] Int. Cl.⁵ ..................... A61B 17/52; B29C 53/02; B29C 65/18
[52] U.S. Cl. ......................................... 156/213; 5/482; 156/215; 156/292; 156/300; 156/306.6; 600/15
[58] Field of Search ............ 156/293, 298, 300, 306.6, 156/580, 581, 583.1, DIG. 21, 212, 213, 215, 292, 297, 91, 499; 128/1.3; 5/482, 495, 502; 600/9, 15

[56] References Cited

U.S. PATENT DOCUMENTS

| 272,904 | 2/1883 | Russell ................... 128/1.3 |
| 1,838,102 | 12/1931 | McGovern ............. 156/212 X |
| 2,521,984 | 9/1950 | Lang ..................... 156/581 |
| 2,681,877 | 6/1954 | Seymour ................ 156/297 |
| 3,520,754 | 7/1970 | Scholl et al. .......... 156/212 X |
| 3,984,272 | 10/1976 | Teed ...................... 156/552 |
| 4,143,435 | 3/1979 | Masuda .................... 5/481 |
| 4,162,672 | 7/1979 | Yazaki ................... 128/1.3 |
| 4,330,892 | 5/1982 | Fukushima ............ 128/1.3 |
| 4,358,495 | 11/1982 | Parker .................... 156/94 |
| 4,391,270 | 7/1983 | Uragami ................ 128/1.3 |
| 4,509,219 | 4/1985 | Yagi ...................... 128/1.3 |
| 4,587,956 | 5/1986 | Griffin et al. .......... 128/1.3 |
| 4,652,481 | 3/1987 | Sjoberg ................ 156/297 X |
| 4,664,736 | 5/1987 | Faasse ................... 156/552 |

FOREIGN PATENT DOCUMENTS

| 1206632 | 6/1986 | Canada ................... 600/15 |
| 0100050 | 2/1984 | European Pat. Off. .... 600/15 |
| 3522667 | 1/1987 | Fed. Rep. of Germany ...... 600/15 |
| 3710123 | 9/1988 | Fed. Rep. of Germany ...... 5/482 |
| 0239239 | 11/1985 | Japan ..................... 5/482 |
| 2168898 | 7/1986 | United Kingdom ...... 128/1.3 |

Primary Examiner—Michael W. Ball
Assistant Examiner—Steven D. Maki
Attorney, Agent, or Firm—Browdy and Neimark

[57] ABSTRACT

A method for fixing a plurality of permanent magnets to an inner cover of bedclothing such as a comforter filled with down and the like comprises the steps of: providing a patch assuming a suitable shape such as a circular shape and the like; applying a bonding-agent sheet to the patch; fixing temporarily a permanent magnet to a center of the bonding-agent sheet to prepare an assembly consisting of the patch, the bonding-agent sheet and the permanent magnet; placing the assembly on a cover of bedclothing in a condition in which the permanent magnet of the assembly abuts on the cover of bedclothing; placing a platen having a hole for receiving the permanent magnet of the assembly therein on the assembly; heating the platen to melt the bonding-agent sheet of the assembly so as to bond the path of the assembly to the cover of bedclothing.

5 Claims, 1 Drawing Sheet

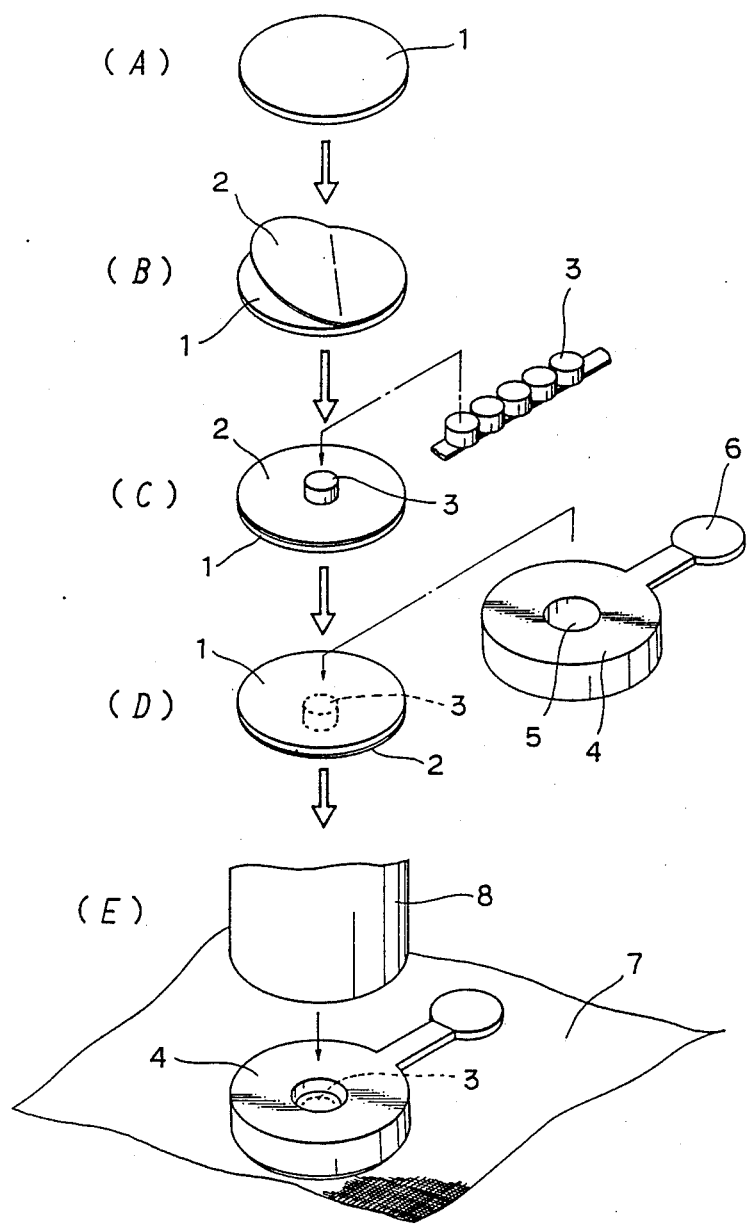

METHOD FOR FIXING PERMANENT MAGNETS TO COVER OF BEDCLOTHING

BACKGROUND OF THE INVENTION

1. Field of the Invention

The present invention relates to a method for fixing a plurality of permanent magnets to an inner side of a cover of bedclothing such as a comforter filled with down and the like.

2. Description of the Prior Art

It is well known that magnetism of a permanent magnet encourages blood flow, causing a user of such permanent magnet to sleep soundly, to recover his spirits and to improve his health. There has been already widely employed a mattress with a plurality of permanent magnets. In addition, it is also known to attach the permanent magnets to a comforter. Hitherto, however, the permanent magnets were fixed to a cover of the comforter by rivetting.

The rivetting is cumbersome work taking too much time, and suffers from the possibility that some pieces of harmful rivet joints remain in the comforter after completion of the rivetting operation of the comforter.

SUMMARY OF THE INVENTION

Therefore, it is an object of the present invention to provide a method for quickly and securely fixing a permanent magnet to a cover of bedclothing in a simple manner.

It is another object of the present invention to provide a method for fixing the permanent magnet to the cover of bedclothing without any fear that some pieces of harmful rivet joints remain in the bedclothing, so as to achieve 100% safety.

Other and further objects, features and advantages of the present invention will appear more fully from the following description.

BRIEF DESCRIPTION OF THE DRAWING

FIG. 1 is a view for illustrating sequential steps of the method of the present invention.

DESCRIPTION OF THE PREFERRED EMBODIMENT

The most preferable embodiment of the present invention will be described in detail with reference to the accompanying drawing.

The method of the present invention is provided with sequential steps having the following order.

Step (A) for providing a patch 1.

The same fabric as that of a cover 7 of bedclothing is cut into a suitable shape such as a circular shape and the like, provided that cutting of such fabric is generally conducted in the following step (B).

Step (B) for applying a bonding-agent sheet 2 to the patch 1.

A plurality of sheets from each of which the patch 1 is constructed and a plurality of the bonding-agent sheets 2 are alternately stacked into a pile which is punched to form a suitable form such as a circular form and the like so as to produce a plurality of the patches 1 and the bonding-agent sheets 2 at once. The patch 1 and the bonding-agent sheet 2 are heated to a temperature of up to a complete-fusion temperature of the bonding-agent sheet 2 so as to be temporarily welded to each other. In this case, the bonding-agent sheet 2 is made of a material having its complete-fusion temperature of about 150° C. and assumes a wafer-like form.

Step (C) for temporarily fixing a permanent magnet 3 to a center of the bonding-agent sheet 2.

The permanent magnet 3 is slightly heated, and then positioned in the bonding-agent sheet 2 so that the permanent magnet 3 is temporarily fixed to the bonding-agent sheet 2 under the effect of a temperature of the thus heated permanent magnet 3, whereby an assembly (1 to 3) consisting of the permanent magnet 3 and the bonding-agent sheet 2 is prepared.

Step (D) for placing the assembly (1 to 3) on the cover 7 of bedclothing in a condition in which the assembly (1 to 3) abuts on the cover 7 at a side of the permanent magnet 3 of the assembly (1 to 3) through the bonding-agent sheet 3 of which assembly a platen 4 is placed on the cover 7.

The assembly (1 to 3) consisting of the permanent magnet 3 and the bonding-agent sheet 2 is placed on the cover 7 of bedclothing in a condition in which the assembly (1 to 3) abuts on the cover 7 at a side of the permanent magnet 3 of the assembly (1 to 3) so that a surface of the permanent magnet 3 is brought into a direct contact with the cover 7 of bedclothing. Then, the platen 4 is placed on the patch 1 of the assembly (1 to 3). The platen 4 is made of a material such as copper and the like having a large thermal conductivity, while shaped into a form similar to that of the patch 1, provided that the platen 4 has a central hole 5 which is larger in diameter than the permanent magnet 3. The central hole 5 of the platen 4 may be constructed of a through-hole as shown in the drawing or a mere concave portion. In addition, the platen 4 may be provided with a grip portion 6 as required. When the platen 4 placed on the patch 1 of the assembly (1 to 3) is slightly depressed, the permanent magnet 3 of the assembly (1 to 3) is received in the central hole 5 of the platen 4, while the patch 1 around the permanent magnet 3 is brought into a close contact with the cover 7 of bedclothing through the bonding-agent sheet 2.

Step (E) for heating the platen 4.

For the case in which a suitable heating means such as a heater and the like is provided in the platen 4, the platen 4 is heated by energizing such heating means. On the other hand, for the case in which the platen 4 is not provided with any heating means as shown in the drawing, an independent heating instrument 8 is brought into contact with the platen 4 to heat the same so that the bonding-agent sheet 2 of the assembly (1 to 3) is heated to its melting point, whereby the bonding-agent sheet 2 of the assembly (1 to 3) is completely melted to cause the patch 1 of the assembly (1 to 3) to be completely welded to the cover 7 of bedclothing in a condition in which the permanent magnet 3 of the assembly (1 to 3) is encapsulated in the patch 1 and the cover 7.

In a manner as described above, a plurality of the permanent magnets 3 are fixed to an inner-side cover 7 of bedclothing, which inner cover 7 abuts on a body of the user. As a result, the permanent magnets 3 are brought into contact with the body of the user through the cover 7 of bedclothing to encourage the user's blood flow during sleeping under the influence of magnetism.

What is claimed is:

1. A method for fixing a permanent magnet to a cover of bedclothing, comprising the steps of:
   provided a patch of material;
   applying a bonding-agent sheet to said patch;

fixing temporarily a permanent magnet to a center portion of said bonding-agent sheet to prepare an assembly consisting of said patch, said bonding-agent sheet and said permanent magnet;

placing said assembly on the cover of said bedclothing so that said permanent magnet of said assembly abuts on said cover of said bedclothing;

placing a platen having a hole for receiving said permanent magent of said assembly therein on said assembly; and heating said platen to melt said bonding-agent sheet of said assembly so as to bond said patch of said assembly to said cover of said bedclothing.

2. The method for fixing the permanent magnet to the cover of said bedclothing as set forth in claim 1, wherein said hole of said platen is constructed of a through-hole.

3. The method for fixing the permanent magnet to the cover of said bedclothing as set forth in claim 1, wherein said hole of said platen is constructed of a concave portion.

4. The method for fixing the permanent magnet to the cover of said bedclothing as set forth in claim 1, wherein a heating means is incorporated in said platen.

5. The method for fixing the permanent magnet to the cover of said bedclothing as set forth in claim 1, wherein the patch has a circular shape.

* * * * *